United States Patent [19]

Baroni et al.

[11] Patent Number: 5,565,474
[45] Date of Patent: Oct. 15, 1996

[54] 1-HETEROARYLAZETIDINES AND -PYRROLIDINES PROCESS FOR THEIR PREPARATION AND PHARMACEUTICAL COMPOSITIONS CONTAINING THEM

[75] Inventors: Marco Baroni, Vanzago; Umberto Guzzi; Antonina Giudice, both of Milan; Marco Landi, Bussero; Vivian Mazza, Legnano, all of Italy

[73] Assignee: SANOFI, Paris, France

[21] Appl. No.: 368,915

[22] Filed: Jan. 5, 1995

Related U.S. Application Data

[62] Division of Ser. No. 127,038, Sep. 24, 1993, Pat. No. 5,410,057.

[30] Foreign Application Priority Data

Sep. 25, 1992 [EP] European Pat. Off. ............. 92402642
Sep. 25, 1992 [EP] European Pat. Off. ............. 92402643

[51] Int. Cl.$^6$ .................... A61K 31/44; C07D 401/04
[52] U.S. Cl. .................... 514/340; 514/255; 514/256; 514/343; 514/210; 544/298; 544/322; 544/334; 544/336; 544/408; 544/409; 546/193; 546/268.1; 546/276.4
[58] Field of Search ....................... 514/255, 256, 514/318, 340, 343; 544/298, 322, 334, 336, 408, 409; 546/193, 275, 281

[56] References Cited

U.S. PATENT DOCUMENTS

| | | | |
|---|---|---|---|
| 4,649,144 | 3/1987 | Matsumoto et al. | 514/300 |
| 5,015,741 | 5/1991 | Osdene et al. | 546/281 |
| 5,138,062 | 8/1992 | Osdene et al. | 546/329 |
| 5,304,555 | 4/1994 | Awaya et al. | 514/228.5 |
| 5,410,057 | 4/1995 | Baroni et al. | 544/334 |

FOREIGN PATENT DOCUMENTS 0421762 4/1991 European Pat. Off. .
0506545 9/1992 European Pat. Off. .

OTHER PUBLICATIONS

Evans et al., *Pharmacology Biochemistry & Behavior*, 40, 4, 1991, 1033–1040.

*Primary Examiner*—Yogendra N. Gupta
*Attorney, Agent, or Firm*—Bacon & Thomas

[57] ABSTRACT

The present invention relates to new 1-heteroarylazetidines and new 1-heteroarylpyrrolidines endowed with 5-HT$_3$ agonist activity of formula (I):

$$R\underset{N}{\underset{\|}{\overset{A}{\fbox{\phantom{XX}}}}}\overset{}{\underset{N}{\diagup}}(CH_2)_n\underset{(CH_2)_m-NR_2R_3}{\overset{R_1}{\diagdown}} \quad (I)$$

in which A is —CH=CH—;

R is hydrogen, halogen, $C_{1-4}$alkyl, $C_{1-4}$alkoxy, $C_{1-4}$alkylthio, cyano, carboxamido, trifluoromethyl, a vinyl group, a formyl group, a carboxyl group in free, salt or esterified form, hydroxyl, hydroxymethyl, mercapto, amino, mono- or di-($C_{1-4}$alkyl)amino, aminomethyl, mono- or di($C_{1-4}$alkyl)aminomethyl, 1-piperido, 1-pyrrolidino, 1-piperazino or 4-($C_{1-4}$alkyl)-1-piperazino, where R may replace any one of the hydrogen atoms of the heteroaryl nucleus;

R$_1$ is hydrogen or a methyl group;

R$_2$ and R$_3$, which are identical or different, are hydrogen or $C_{1-4}$alkyl;

n is 1 or 2; m is 0 or 1; and m+n≧2;

and addition salts with inorganic or organic acids of the compounds of formula (I). The invention also relates to pharmaceutical compositions containing these compounds, as well as to methods of treatment or prophylaxis of disorders which involve the peripheral or central serotoninergic systems.

18 Claims, No Drawings

1-HETEROARYLAZETIDINES AND -PYRROLIDINES PROCESS FOR THEIR PREPARATION AND PHARMACEUTICAL COMPOSITIONS CONTAINING THEM

This application is a Division of application Ser. No. 08/127,038, filed Sep. 24, 1993, now U.S. Pat. No. 5,410,057.

The present invention relates to new 1-heteroaryl azetidine and pyrrolidine derivatives endowed with agonist activity to the 5-HT$_3$ receptors.

The invention also relates to the process for the preparation of these compounds, the new intermediates obtained by this process, the application of the said new compounds as drugs and the pharmaceutical compositions containing them.

Pyrazine, pyrimidine and pyridazine derivatives which can be substituted inter alia by a 2- or 3-azetidinyl radical have been described in European Patent Application EP-A-327155 as stimulants of central muscarine receptors.

Quinolines and naphthyridines substituted by a 1-azetidinyl radical, which are useful as bactericides, have been described in European Patent Applications EP-A-106489 and EP-A-153163.

Azetidine derivatives substituted by a heterocyclic ring on the nitrogen atom and by a substituted amino group in position 3 have been claimed in German Patent Application DE-A-2241097, where they are described as analgesics and antiinflammatory agents.

European Patent EP-155870 mentions the use of 3-aminoazetidine, which is claimed in the preparation of 3-amino-1-(6-chloropyrid-2-yl)azetidine endowed with anorexigenic activity.

3-Pyridinecarboxylic acid derivatives substituted by a fluorophenylamino group in position 2, by a fluorine atom in position 5 and inter alia by an optionally protected 3-aminopyrrolidino group in position 6 are claimed as intermediates for the synthesis of bactericidal 1,8-naphthyridines in patent BE-904086.

Japanese Patent Application JP 62033176 (WPI 87-082820) describes 3-nicotinoylacetic acid derivatives substituted by a chlorine atom in position 2, by a fluorine atom in position 5 and by, inter alia, an optionally substituted cyclic amino group in position 6, as intermediates to naphthyridines, while derivatives of 2-pyridylaminomethylenepropanedioic acid, also useful as intermediates to naphthyridines, are described in EP-376870.

Finally, 3-amino-5-phenyl-1-(2-pyridyl)pyrrolidine, a possible intermediate to histamine antagonists, as well as its stereoselective synthesis, have been described in J. Heterocycl. Chem., 1973, 10 (5), 747–753.

It has now been found that certain 1-heteroarylazetidine and -pyrrolidine derivatives in which the nitrogen atom is bonded to an optionally substituted pyridine, pyrazine or pyrimidine and the carbon in position 3 carries an aminomethyl or optionally alkylated amino group have a highly advantageous novel biochemical activity, showing themselves to be selective agonists for the serotonin 5-HT$_3$ receptors.

More particularly, therefore, as first subject, the present invention refers to the new 1-heteroarylazetidines or pyrrolidines corresponding to the following formula (I)

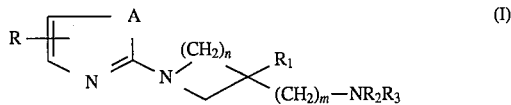

in which

A denotes a —CH=CH—, —CH=N— or —N=CH— group;

R denotes a hydrogen atom, a halogen atom, a $C_1$–$C_4$ alkyl, $C_1$–$C_4$ alkoxy or $C_1$–$C_4$ alkylthio group, a cyano, carboxamido, trifluoromethyl, vinyl or formyl group, a carboxyl group in free, salt or esterified form, a hydroxyl, hydroxymethyl or mercapto group or an amino, mono- or di($C_1$–$C_4$ alkyl)amino, aminomethyl, mono- or di($C_1$–$C_4$ alkyl)aminomethyl, 1-piperidino, 1-pyrrolidino, 1-piperazino or 4-($C_1$–$C_4$ alkyl)-1-piperazino group, it being possible for this group R to replace any one of the hydrogen atoms of the heteroaryl nucleus;

$R_1$ is a hydrogen atom or a methyl group;

$R_2$ and $R_3$, which are identical or different, denote a hydrogen atom or a $C_1$–$C_4$ alkyl group;

n is 1 or 2, m is 0 or 1 and m+n≧2 it being possible for the said compounds to be in any of the optionally possible isomeric, racemic, enantiomeric and diastereoisomeric forms, and in the form of addition salts with inorganic or organic acids.

The compounds of formula (I) as defined above and their addition salts with pharmaceutically acceptable acids exhibit advantageous pharmacological properties. More particularly, these products are endowed with selective agonist properties for the serotonin 5-HT$_3$ receptors. These properties justify their application in therapeutics for the preparation of medications intended for the prophylaxis and for the treatment of disorders of the serotoninergic system when it is desired to have a selective agonist action mediated by the 5-HT$_3$ receptors.

In the products of formula (I) and in what follows:

the term "$C_1$–$C_4$ alkyl" denotes a linear or branched alkyl radical containing from 1 to 4 carbon atoms, preferably methyl, ethyl, n-propyl and isopropyl radicals, but also n-butyl, isobutyl, sec-butyl and tert-butyl radicals;

the term "$C_1$–$C_4$ alkoxy" denotes an alkoxy radical with a straight or branched chain containing from 1 to 4 carbon atoms, preferably methoxy and ethoxy radicals, but also propoxy, isopropoxy and linear, secondary or tertiary butoxy radicals;

the term "$C_1$–$C_4$ alkylthio" denotes an alkylthio radical with a linear or branched chain containing from 1 to 4 carbon atoms and preferably methylthio, ethylthio and isopropylthio radicals;

the term "halogen atom" preferably denotes the chlorine or bromine atom but may also represent a fluorine or iodine atom;

the term "esterified carboxyl" preferably denotes a lower alkoxycarbonyl group such as methoxycarbonyl, ethoxycarbonyl and tert-butoxycarbonyl, or a benzyloxycarbonyl group, whereas the term "carboxyl in salt form" preferably denotes a carboxyl group converted into salt with an inorganic base such as, for example, one equivalent of sodium, potassium, calcium, magnesium or ammonium, or an organic base such as, for example, methylamine, propylamine, trimethylamine, N,N-dimethylethanol-amine, tri-(hydroxymethyl)aminomethane, pyridine, picoline, dicyclohexylamine, benzylamine, procaine, lysine, arginine, N-methylglucamine or a compound of formula (I).

The addition salts of the compounds of formula (I) with inorganic or organic acids may be, for example, the salts formed with hydrochloric, hydrobromic, hydriodic, nitric, sulphuric, oxalic, phosphoric, propionic, acetic, formic, benzoic, maleic, fumaric, succinic, tartaric, citric, oxalic, glyoxylic, aspartic and ascorbic acids, sulphonic acids such as methanesulphonic, ethanesulphonic, methanedisulphonic and benzenesulphonic acid and the like. Salts formed with hydrochloric acid are preferred in particular.

A preferred class of compounds of formula (I) comprises the compounds of formula (Ia) which corresponds to the formula (I) where n and m are 1

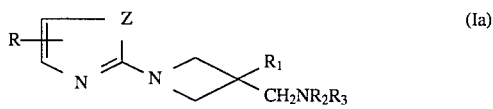 (Ia)

and R, A, $R_1$, $R_2$ and $R_3$ are as defined above.

A particularly preferred group of compounds of formula (Ia) according to the present invention comprises the compounds of formula (Ia) in which A denotes a —CH=CH— (pyridine derivatives) or —N=CH— (pyrazine derivatives) group, R, $R_2$ and $R_3$ are as defined above and $R_1$ is hydrogen, and their addition salts with acids.

Still more preferred are the compounds of formula (Ia) in which A, $R_1$, $R_2$ and $R_3$ are as defined above in the definition of a preferred group and R denotes a hydrogen or halogen atom, a $C_1$-$C_4$ alkyl, $C_1$-$C_4$ alkoxy, cyano, carboxamido, trifluoromethyl, vinyl or formyl group or carboxyl in free, salt or esterified form, or an amino group, and their addition salts with acids.

Particularly preferred are the compounds of formula (Ia) in which A denotes a —CH=CH— group, R denotes a chlorine or bromine atom in positions 3, 5 or 6, $R_1$ is a hydrogen atom and $R_2$ and $R_3$ are identical and denote a hydrogen atom or a $C_1$-$C_4$ alkyl group, and their addition salts with acids.

Another particular class of compounds of formula (I) comprises the compounds of formula (Ib) which corresponds to the formula (I) where n is 2

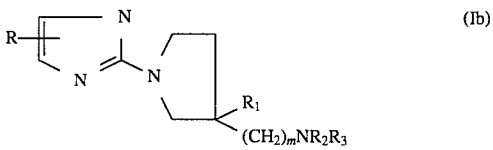 (Ib)

m is 0 or 1 and all the other substituents R, A, $R_1$, $R_2$ and $R_3$ are as defined above.

A particularly preferred group of compounds of formula (Ib) according to the present invention comprises the compounds of formula (Ib) in which A denotes a —CH=CH— (pyridine derivatives) or —N=CH— (pyrazine derivatives) group, m, R, $R_2$ and $R_3$ are as defined above and $R_1$ is hydrogen, and their addition salts with acids.

Still more preferred are the compounds of formula (Ib) in which m, A, $R_1$, $R_2$ and $R_3$ are as defined above in the definition of a preferred group, and R denotes a hydrogen or halogen atom, a $C_1$-$C_4$ alkyl, $C_1$-$C_4$ alkoxy, cyano, carboxamido, trifluoromethyl, vinyl, formyl, carboxyl in free, salt or esterified form or an amino group, and their addition salts with acids.

Particularly preferred are the compounds of formula (Ib) in which A denotes a —CH=CH— group, R denotes a chlorine or bromine atom in positions 3, 5 or 6, m is 0, $R_1$ is a hydrogen atom and $R_2$ and $R_3$ are identical and denote a hydrogen atom or a $C_1$-$C_4$ alkyl group, and their addition salts with acids.

The compounds of formula (I) of the present invention can be prepared from a heterocyclic compound of formula (II)

 (II)

in which A has the meaning given above, Hal denotes a halogen atom, chlorine, bromine and iodine being preferred, and R' corresponds to R or to an R group protected by an easily removable suitable protective group; and from an azetidine or pyrrolidine derivative of formula (III):

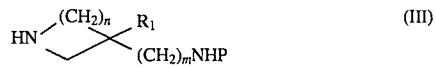 (III)

in which n, m and $R_1$ are as defined above and P denotes a temporary protective group for the amino group which is suitably chosen.

The starting compounds of formula (II) are generally products which are available commercially or which can be prepared in the laboratory by very simple reactions which are well known to a person skilled in the art.

The starting compounds of formula (III) where n is 1 can be prepared from 1-benzhydrylazetidin-3-ol or 1-benzhydryl-3-methylazetidin-3-ol by conversion of the hydroxyl group into a mesyloxy group, replacement of the latter with a cyano group, reduction of the cyano group to aminomethyl, protection of the amino group with a suitable group P and selective removal of the benzhydryl group by catalytic hydrogenation. The starting pyrrolidines of formula (III) where n is 2 and m is 0 can be prepared from 1-benzyl-3-pyrrolidone (J. Org. Chem., 1965, 30, 740). When $R_1$ is a hydrogen atom, 1-benzyl-3-pyrrolidone is converted into the corresponding oxime by reaction with hydroxylamine. The oxime functional group is then reduced with the aid of a mixed hydride such as $LiAlH_4$, the primary amino group which is formed is protected by introducing the protective group P and the 1-benzyl group is removed by catalytic hydrogenation with platinum or palladium catalysts.

When $R_1$ denotes a methyl group, 1-benzyl-3-methyl-3-acetylaminopyrrolidine can be obtained by following the method described in EP-132845 (Example 7) and, optionally, before removing the benzyl group by catalytic hydrogenation, by removing the acetyl group by hydrolysis and by introducing a different protective group P.

The compounds of formula (III) where n is 2 and m is 1 are easily prepared from 1-benzyl-3-pyrrolidinol, which is a commercial product, and from 1-benzyl-3-methyl-3-pyrrolidinol (EP-132845—Example 7) by conversion into the corresponding mesyl derivative, replacement of the mesyloxy group with a cyano group and reduction of the cyano group to aminomethyl with the aid of $LiAlH_4$ finally followed by deprotection by catalytic hydrogenation with platinum catalysts.

The reaction between the compound of formula (II) and the derivative of formula (III) produces an intermediate compound of formula (IV)

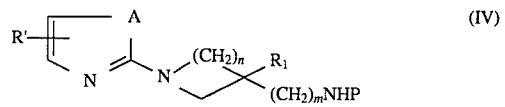 (IV)

in which n, m, R', A, $R_1$ and P are as defined above, and the successive removal of the protective group(s) produces the compound of formula (I) where n, m, R, A and $R_1$ are as defined above and $R_2$ and $R_3$ are two hydrogen atoms. When it is intended to obtain a compound of formula (I) where $R_2$ and/or $R_3$ are other than hydrogen, this is followed by the mono- or dialkylation of the amino group using known conventional methods.

Under preferred conditions of implementation of the invention the above process is carried out as follows.

The reaction of the compound of formula (II) with the compound of formula (III) is conducted in an organic solvent such as an alcohol, preferably n-butanol, n-pentanol or n-hexanol, in dimethylformamide, dimethyl sulphoxide, sulpholane, acetonitrile, pyridine and similar solvents, at a temperature which is generally between 50° C. and 200° C., in the presence of an alkaline condensing agent such as an alkali metal hydroxide, carbonate or bicarbonate or of a tertiary amine. After 20 to 120 hours the reaction is complete and the intermediate compound of formula (IV) thus obtained is isolated by the usual techniques.

The protective group(s) is (are) then removed in the usual conditions which are known to a person skilled in the art and which depend on the protective group chosen.

The preferred protective groups for the amino functional group are t-alkoxycarbonyl groups such as t-butoxycarbonyl (BOC) or t-amyloxycarbonyl (AOC), the BOC group being particularly preferred. The removal of these groups is therefore easily performed by acidic hydrolysis using methods which are well known in the literature and especially by the action of trifluoro-acetic acid or of hydrochloric acid in an alcoholic solvent.

A protective group for the amino functional group which may also be employed is the acetyl group, which can be removed using well-known acidic or basic hydrolysis techniques, for example by heating the blocked intermediate of formula (IV) in an aqueous solution of an inorganic or organic acid, preferably hydrochloric acid, or by treating it with an inorganic base, preferably sodium hydroxide.

The various reactive functional groups which are optionally present in some starting compounds of formula (II) can be protected, if necessary or appropriate; these are, for example, hydroxyl, amino, carboxyl and mercapto groups, which can be protected conventionally. As an example of protection for the hydroxyl group there may be mentioned, nonexhaustively, silyl radicals such as trimethylsilyl and t-butyldimethylsilyl and etherifying groups such as the tetrahydropyranyl group.

The amino substituent of the heterocyclic nucleus can be protected, as indicated above, with a t-alkoxycarbonyl group.

The carboxyl group can be protected in the form of an easily splittable ester such as a benzyl or t-butyl ester or of esters which are known in peptide chemistry. It can also be protected in the form of a corresponding protected alcohol and then regenerated by oxidation.

Finally, the mercapto group can be protected by forming a mixed or symmetrical disulphide.

Other protective groups which are appropriate in the envisaged reaction conditions and methods for removing them at the end of the reaction are described in the literature (see, for example, D. Barton and W. C. Ollis, Comprehensive Organic Chemistry, vol. 5, pp. 323–331 and the references to be found mentioned therein) and are well known to a person skilled in the art, who is therefore capable of choosing the most appropriate ones depending on the circumstances.

A compound of formula (I) is thus obtained in which $R_2$ and $R_3$ are both hydrogen. This compound can therefore be isolated and/or converted into one of its addition salts by treatment with a hydroalcoholic or organic solution of the acid forming the salt.

If it is intended to obtain a compound of formula (I) in which one of $R_2$ and $R_3$ denotes an alkyl group, the primary amine thus obtained is condensed with the appropriately chosen aldehyde or ketone by forming an intermediate Schiff base, which is reduced using hydrides which are well known to a person skilled in the art, typically sodium cyanoborohydride.

This secondary amino group can then be subsequently alkylated by conventional methods for alkylating amino groups, for example by reaction with an alkyl halide, preferably an alkyl iodide. Dialkyl derivatives where $R_2$ and $R_3$ differ from each other can thus be obtained.

When it is intended to obtain a compound of formula (I) where $R_2$ and $R_3$ are identical and denote an alkyl group, the conventional method is followed directly using at least the stoichiometric quantity of alkylating agent.

The compounds of formula (Ib) of the present invention contain at least one chiral carbon atom, that carrying the $(CH_2)_m$—$NR_2R_3$ group, and exist, therefore, in the form of racemates or enantiomers.

The pure enantiomers can be obtained either by starting with a compound of formula (III) in optically active form or by resolving the racemic mixture of the compound (Ib), for example by means of a resolving agent such as a derivative of tartaric acid or of other optically active acids.

The starting compounds of formula (III), in their turn, can be obtained in an optically active form by resolving the racemates using conventional methods which are known to a person skilled in the art, such as, for example, the formation of diastereoisomeric salts with optically active acids or the use of chiral chromatography columns.

If the substituents R, $R_2$ and $R_3$ contain additional chiral atoms then a number of isomeric forms are possible and the compounds (Ib) could be in the form of racemates, enantiomers or diastereoisomers, all of which isomeric forms are included within the subject matter of the present invention.

The possible optically active forms of the products of formula (Ia) which exist when $R_1$ is a methyl group and/or the substituents R, $R_2$ and $R_3$ contain chiral atoms, can be prepared by resolving the racemates by the usual methods known to a person skilled in the art, such as, for example, the formation of diastereoisomeric salts or the use of chiral chromatography columns.

As an alternative to the general method described above or, preferably, when the starting compound of formula (II) is not a product that is available commercially or easily prepared, some compounds of formula (I) can be obtained by modifying the group R in other compounds (I) or in their intermediates (IV) using reactions which are well known in conventional chemistry.

For example, when it is intended to obtain a compound of formula (I) where R is a vinyl group, it is possible to start with a compound (II) where R is a halogen atom, thus to obtain an intermediate compound (IV) where R is a halogen atom and then to replace this atom with a vinyl group, for example by reaction with a tin vinyl derivative such as tributylvinyltin, in the presence of tetrakis(triphenylphosphine)palladium. The nitrogen atom of the amino group can then be deblocked and optionally alkylated thus to obtain compounds (I) where A, $R_1$, $R_2$ and $R_3$ are as defined above and R is a vinyl group. Alternatively, before deblocking the amino group, the vinyl group can be oxidized with, for example, an alkali metal periodate in the presence of osmium tetraoxide as catalyst and to obtain the corresponding compounds where R is a formyl group.

In their turn, these latter compounds can be oxidized, for example with the Jones reactant, which is made up of a solution of chromic anhydride in sulphuric acid, or with alkali metal chlorite, giving the corresponding carboxylic acids. Esterification of the latter, for example with the corresponding alcohol in the presence of a dehydrating agent, produces the desired esters.

Similarly, the esterified carboxyl radical can be reduced to a hydroxymethyl radical in the usual conditions which are known to a person skilled in the art, such as especially by the action of lithium aluminium hydride, diisobutylaluminium hydride or other reducing agents which are known to a person skilled in the art.

The optional methoxy substituent of the products described above can, if desired, be converted into a hydroxyl group, for example with boron tribromide in an inert organic solvent such as, for example, methylene chloride.

A halogen atom on the heteroaromatic nucleus can also be replaced with a substituted amino radical, for example by treating the halogen compound with a secondary amine such as dialkylamines or cyclic amines, at ambient temperature in a solvent such as an alcohol, especially ethanol or methanol.

Similarly, a halogen atom on the heteroaromatic nucleus can be converted into an alkoxy, e.g. methoxy, group by reaction with a nucleophile such as alkoxide, e.g. methoxide.

Similarly, this halogen atom can be converted into a cyano group by reaction, for example, with tributylcyanotin in the presence of tetrakis(triphenylphosphine)palladium. Partial hydration of compounds (I) or (IV) where R is a cyano group gives the corresponding compounds where R is a carboxamido group. This hydrolysis of the cyano group to a carboxamido group can be conducted under controlled acidic catalysis conditions or, more appropriately, under mild basic conditions in the presence of hydrogen peroxide as catalyst.

From the intermediate compounds of formula (IV) where R is a cyano or carboxamido group it is then possible to obtain the corresponding compounds where R is an aminomethyl group by reduction with a mixed hydride such as, for example, lithium aluminium hydride and its alkoxylated derivatives.

The amino group can then be mono- or dialkylated by the methods described above.

Other reactions, which are well-known in conventional chemistry, can be employed to convert one substituent R into another, either in the final products (I) or in the protected intermediates (IV); all methods for preparing the compounds (I) involving these reactions are therefore included within the concept of the present invention.

A subsequent subject of the present invention is therefore a process for the preparation of a compound of formula (I)

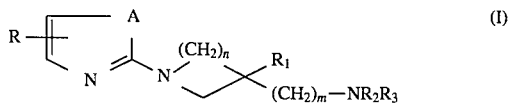

in which

A denotes a —CH=CH—, —CH=N— or —N=CH— group;

R denotes a hydrogen atom, a halogen atom, a $C_1$–$C_4$ alkyl, $C_1$–$C_4$ alkoxy or $C_1$–$C_4$ alkylthio group, a cyano, carboxamido, trifluoromethyl, vinyl or formyl group, a carboxyl group in free, salt or esterified form, a hydroxyl, hydroxymethyl or mercapto group, an amino, mono- or di($C_1$–$C_4$ alkyl)amino, aminomethyl, mono- or di($C_1$–$C_4$ alkyl)aminomethyl, 1-piperidino, 1-pyrrolidino, 1-piperazino or 4-($C_1$–$C_4$ alkyl)-1-piperazino group, it being possible for this group R to substitute any one of the hydrogen atoms of the heteroaryl nucleus;

$R_1$ is a hydrogen atom or a methyl group;

$R_2$ and $R_3$, which are identical or different, denote a hydrogen atom or a $C_1$–$C_4$ alkyl group;

n is 1 or 2; m is 0 or 1 and n+m≧2 characterized in that a halosubstituted heterocyclic compound of formula (II)

in which A has the meaning given above, R' corresponds to R or to a group R protected by an easily removable appropriate protective group and Hal denotes a halogen atom, is reacted with an azetidine or pyrrolidine of formula (III)

in which n, m and $R_1$ are as defined above and P is a temporary protective group for the amino group which is suitably chosen, to obtain an intermediate compound of formula (IV)

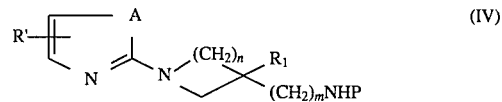

in which n, m, R', A, $R_1$ and P are as defined above, the protective groups present are next removed thus to obtain a compound of formula (I) where n, m, A, R and $R_1$ are as defined above and $R_2$ and $R_3$ are hydrogen, and when it is intended to obtain a compound of formula (I) in which $R_2$ and/or $R_3$ are other than hydrogen, the nitrogen atom is alkylated using suitable methods; and the final product is optionally converted into one of its addition salts with inorganic or organic acids; and optionally after each stage a substituent R may be converted into another one by reactions which are known per se.

The compounds of formula (IV) where n, m, R', A, $R_1$ and P are as defined above are new industrial products and intermediates necessary for the preparation of the compounds of formula (I) and therefore represent a specific further subject of the present invention.

The compounds of formula (I) as defined above and their addition salts with pharmaceutically acceptable acids exhibit advantageous pharmacological properties.

These products are endowed with selective agonist properties for the serotonin 5-$HT_3$ receptor.

The affinity of the compounds of formula (I) for the 5-$HT_3$ receptors has been demonstrated with the aid of in-vitro binding tests by employing the 5-$HT_3$ binding sites present in the cerebral cortex of the rat (G. J. Kilpatrick, B. J. Jones and M. B. Tyers. Identification and distribution of 5-$HT_3$ receptors in rat brain using radioligand binding. Nature, 1987; 330: 746-8) and, as labelled ligand, [$^3$H]-BRL 43694 (granisetron), a powerful and specific antagonist of the 5-$HT_3$ receptors.

The preparation of the membranes and the binding test were performed using the method described by Nelson and Thomas (D. R. Nelson and D. R. Thomas. [$^3$H]-BRL 43694 (granisetron), a specific ligand for 5$HT_3$ binding sites in rat brain cortical membranes. Blochem. Pharmacol., 1989; 38: 1693-5).

The results have been evaluated with the "Accufit saturation" nonlinear fitting methods in the case of the saturation studies (H. A. Feldman. Mathematical theory of complex ligand-binding systems at equilibrium: some methods of parameter fitting. Analyt. Blochem., 1972; 48: 317-38) and "Accufit competition" in the case of the displacement studies (H. A. Feldman, D. Rodbard and D. Levine. Mathematical theory of cross reactive radioimmunoassay and ligand-binding systems at equilibria. Analyt. Biochem., 1972; 45: 530-56).

To obtain the affinities of the compounds a concentration of 0.5 nM of [$^3$H]-BRL 43694 was employed in the competition studies.

In these in-vitro tests the compounds of formula (I) have shown themselves to be generally very powerful in the displacement of [$^3$H]-BRL 43694.

The affinity has been confirmed and the agonist activity in respect of the 5-HT$_3$ receptors has been demonstrated also by virtue of studies in the anaesthetized rat, in particular by administering the compounds intravenously and observing the fugitive decrease in the cardiac frequency (Bezold-Jarisch effect) whose intensity varies according to the dose.

This effect is inhibited by the selective anta-gonists for the 5-HT$_3$ receptors (for example ICS 205930 and zacopride), whereas it is not inhibited by the antagonists for the D receptors of serotonin (for example methysergide).

More particularly, the Bezold-Jarisch effect produced by the compounds of formula (I) has been evaluated by employing Sprague-Dawley rats between 200 and 300 g in weight, anaesthetized with an intraperitoneal dose of 1.25 g/kg of urethane. The arterial pressure is recorded at a carotid artery and the cardiac frequency evaluated using the pulse frequency with the aid of a cardiotachymeter. A catheter is placed in the jugular vein for administering the substances.

Different doses of the compounds to be tested are administered intravenously in a volume of 0.5 ml/kg.

The bradycardia caused by each dose is expressed as inhibition as a percentage of the basal frequency. It is thus possible to calculate the ED$_{50}$, that is to say the dose which decreases the cardiac frequency by 50% in the treated animals.

The most advantageous compounds have shown results, expressed as ED$_{50}$, which are between 0.5 and 10 µg/kg.

These properties justify the application of new compounds of formula (I) according to the invention in therapeutics in the treatment of disorders which involve either the peripheral or the central serotoninergic system when it is desired to have a selective agonist action mediated by the 5-HT$_3$ receptors. It is possible, for example, to envisage the therapeutic use of these products in the treatment of dysthimic disorders, or else in cases of anxiety or of psychotic disorders.

The use of these products in the treatment of disorders of intestinal motoricity can also be envisaged, in particular in the treatment of constipation.

A further subject of the invention is therefore the use of the compounds of formula (I) where n, m, R, A, R$_1$, R$_2$ and R$_3$ have the meanings given above, and of their pharmaceutically acceptable salts, as drugs.

The invention extends to the pharmaceutical compositions containing, as active principle, at least one of the compounds as defined above.

These pharmaceutical compositions can be administered orally, rectally or parenterally.

These compositions can be solid or liquid and may take any pharmaceutical form commonly employed in human medicine such as, for example, simple or sugar-coated tablets, gelatin capsules, granulates, solutions or suspensions for oral administration, suppositories and injectable preparations; they are prepared by the usual methods. The active principle can be incorporated therein in excipients which are usually employed in these pharmaceutical compositions, such as talc, gum arabic, lactose, starch, magnesium stearate, cacao butter, aqueous or nonaqueous carriers, fatty substances of animal or vegetable origin, paraffinic derivatives, glycols, various wetting, dispersing or emulsifying agents, stabilizers and the like.

The usual posology, which can vary depending on the specific product employed, the conditions and the weight of the subject being treated, the disorder in question and the method of administration, can be suitably between 1 and 1000 mg daily in an adult.

The following examples illustrate the invention without, however, limiting it.

PREPARATION I a) A mixture of 50 g (0.157 mol) of 1-benzhydryl-3-mesyloxyazetidine (J. Org. Chem. 1972, 37, 3953–3955) and 23.5 g (0.479 mol) of sodium cyanide in 340 ml of dimethylformamide and 43 ml of water is heated to 60° C. for 5 hours. The reaction mixture is left at ambient temperature overnight and is then poured into 2000 ml of water/ice. The solid product is recovered by filtration and is purified by being suspended in 800 ml of water and being filtered. The product thus obtained is dried and crystallized from isopropyl ether to obtain 20 g of 1-benzhydryl-3-azetidinecarbonitrile. M.p. 142°–146° C.

b) 0.37 g (0.008 mol) of lithium aluminium hydride in 40 ml of anhydrous ethyl ether are stirred at ambient temperature and 1 g (0.004 mol) of the compound obtained in stage a) above is added to it portionwise over 10 minutes. After refluxing for 2.5 hours the mixture is cooled and diluted with water. The organic phase is separated off, washed with water and dried. 3-Aminomethyl-1-benzhydrylazetidine (1.15 g) hydrochloride precipitates on addition of isopropanol saturated with hydrogen chloride. M.p. 202°–204° C.

c) A solution of 7.5 ml (0.073 mol) of acetic anhydride in 10 ml of ethyl acetate is added slowly to a mixture of 18 g (0.0713 mol) of 3-aminomethyl-1-benzhydrylazetidine obtained from the corresponding hydrochloride of stage b) by neutralization with 10% sodium hydroxide, extraction with ethyl acetate and evaporation of the solvent, in 150 ml of ethyl acetate. The reaction mixture is stirred at ambient temperature for 1 h, is cooled and 50 ml of 2N NaOH are added to it with vigorous stirring. After 10 minutes stirring, the organic phase is separated off, is washed with water and is dried and concentrated at reduced pressure to obtain 20 g of 3-acetylaminomethyl-1-benzhydrylazetidine. M.p. 117°–119° C.

d) 19.5 g (0.0662 mol) of the compound obtained in stage c), 200 ml of 95% ethanol, 3.91 g of 20% Pd(OH)$_2$ on carbon and 5.4 ml of concentrated hydrochloric acid are charged into a hydrogenation apparatus. They are placed under a hydrogen atmosphere and hydrogenated at ambient pressure, at 40° C., for 3 hours. After filtering, the filtrate is concentrated by evaporation at reduced pressure and the oily residue is taken up with benzene (2×50 ml) and then with acetone. The organic solvent is evaporated at reduced pressure to obtain 10 g of 3-acetylaminomethylazetidine hydrochloride.

PREPARATION II a) A solution of 31 g (0.0142 mol) of di-tert-butyl dicarbonate in 70 ml of anhydrous chloroform is added dropwise to a solution of 35.9 g (0.142 mol) of 3-aminomethyl-1-benzhydrylazetidine in 360 ml of anhydrous chloroform under nitrogen atmosphere and is left stirred at ambient temperature for 6 hours. The solvent is evaporated off and the oily residue is taken up with a small quantity of an ethyl ether/hexane mixture. The solid product thus obtained is filtered off and dried in the oven to obtain 36.5 g of 1-benzhydryl-3-tert-butoxycarbonylaminomethylazetidine.

M.p. 108°–110° C.

b) A mixture of 36.5 g (0.103 mol) of this compound and 10 g of 20% Pd(OH)$_2$ on carbon in 650 ml of absolute ethanol is heated to 50°–60° C. under a hydrogen atmosphere. After 4 hours, when the theoretical quantity of hydrogen has been consumed, the catalyst is removed by filtration and the filtrate is concentrated at reduced pressure. The solid product thus obtained is taken up with isopropyl ether, is filtered and is dried in the oven to obtain 19.8 g of 3-tert-butoxycarbonylaminomethylazetidine. M.p. 112°–114° C.

PREPARATION III a) 10 g (0.0394 mol) of 1-benzhydryl-3-methylazetidin-3-ol (S. S. Chattergee and A. Shoeb, Synthesis 1973, p. 153–154) are dissolved in 100 ml of anhydrous pyridine, the mixture is cooled to –20° C. and 7.3 g (0.063 mol) of methanesulphonyl chloride are added dropwise. The temperature is kept below –10° C., stirring is carried out at this temperature for 1 hour and the reaction mixture is left between 0° C. and 3° C. for two days. It is poured into 600 ml of water/ice, the precipitate is recovered by filtration and is washed with water. After drying in the oven at 50° C. for 2 hours the product is taken up in isopropyl ether (100 ml), is filtered and is dried in the oven at 50° C. overnight to obtain approximately 10 g of 1-benzhydryl-3-methanesulphonyloxy-3-methylazetidine.

b) 3-Acetylaminomethyl-3-methylazetidine hydrochloride is obtained by operating as described in PREPARATION I, stages a), b), c) and d), but starting with the compound obtained in stage a) above.

PREPARATION IV a) A solution of 2.6 g (0.025 mol) of diisopropylamine in 80 ml of anhydrous tetrahydrofuran is cooled to –78° C. under nitrogen and 10 ml of a 2M solution of n-BuLi in n-hexane are added to it with great care. Stirring is carried out for 30 minutes and a solution of 6.2 g (0.025 mol) of 1-benzhydrylazetidine-3-carbonitrile obtained in stage a) of PREPARATION I in 30 ml of tetrahydrofuran is added to it. After 1 hour's stirring, a solution of 7.0 g (0.05 mol) of methyl iodide in 10 ml of tetrahydrofuran is added dropwise. Stirring is carried out for 1 hour and the reaction mixture is allowed to warm up to ambient temperature. It is left to stand overnight and the basic solution is neutralized by addition of approximately 100 ml of a 20% solution of NH$_4$Cl and a few drops of concentrated HCl. The product is extracted with methylene chloride and the organic phase is concentrated to obtain 6.0 g of 1-benzhydryl-3-methyl-3-azetidinecarbonitrile which is crystallized from n-hexane. M.p. 78°–80° C.

b) 4.07 g (0.015 mol) of the compound obtained in stage a) above are added portionwise to a suspension of 0.85 g (0.0225 mol) of LiAlH$_4$ in 180 ml of ethyl ether while the temperature is controlled. The mixture is refluxed for 2.5 hours, is cooled in an ice bath and approximately 170 ml of water are added to it. It is filtered and the filtrate is washed with water, is dried over sodium sulphate and is concentrated at reduced pressure to obtain 2.7 g of 3-aminomethyl-1-benzhydryl-3-methylazetidine in the form of yellow semi-solid oil. The corresponding addition salt with oxalic acid, crystallized from acetone, has an m.p. of 168°–170° C.

c) A solution of 2.16 g (0.0096 mol) of di-tert-butyl dicarbonate in 15 ml of chloroform is added dropwise to a solution of 2.57 g (0.0096 mol) of 3-aminomethyl-1-benzhydryl-3-methylazetidine in 30 ml of anhydrous chloroform under a nitrogen atmosphere. The mixture is stirred at ambient temperature under nitrogen overnight and is evaporated to dryness to obtain 2.7 g of 1-benzhydryl-3-tert-butoxycarbonylaminomethyl-3-methylazetidine. M.p. 106°–107° C.

d) A mixture of 4.2 g (0.0115 mol) of the compound obtained in the preceding stage, 0.5 g of 20% Pd(OH)$_2$ on carbon, 70 ml of absolute ethanol and 4 ml of ethanol saturated with hydrogen chloride is hydrogenated at atmospheric pressure and 50°–60° C. When the theoretical quantity of hydrogen has been consumed the product is filtered and the filtrate is concentrated to dryness. The residue is treated with 10 ml of acetone and is ground wet and filtered to obtain 1.5 g of 3-tert-butoxycarbonylaminomethyl-3-methylazetidine. M.p. 189°–191° C.

PREPARATION V a) 1-Benzyl-3-cyanopyrrolidine 4.8 g (0.004 mol) of methanesulphonyl chloride are added dropwise to a solution of 5 g (0.028 mol) of 1-benzyl-3-pyrrolidinol in 65 ml of anhydrous pyridine cooled to –20° C. Stirring is carried out for 1 hour, the temperature is allowed to rise to the ambient value and stirring is continued for 5 hours. The product is poured onto ice and extracted with methylene chloride. The organic phase is evaporated in vacuum, producing 7.9 g of a crude oil, which is purified by chromatography and eluting with a 98/2 CH$_2$Cl$_2$/MeOH mixture. 4.2 g (0.0166 mol) of the mesylate are obtained and are dissolved in 25 ml of dimethylformamide. A solution of 3.2 g (0.05 mol) of potassium cyanide in 6 ml of water is added to the solution thus obtained and is heated to approximately 70° C. for 8 hours. After standing overnight, the product is poured onto ice and is extracted with ethyl acetate. The organic phase is washed with water, is dried over Na$_2$SO$_4$ and is concentrated in vacuum producing 2.6 g of an oily product, which is purified by chromatography on a column (eluent: 7/3 cyclohexane/ethyl acetate). 1.3 g of the compound referred to in the title are obtained. B.p.=100° C./0.3 mmHg.

b) 1-Benzyl-3-aminomethylpyrrolidine 3.49 g (0.019 ml) of the compound obtained in stage a) above are added to a solution of 1.07 g (0.028 mol) of LiAlH$_4$ in 140 ml of anhydrous ethyl ether, with stirring so as to maintain a constant temperature. The mixture is refluxed for 3 hours, is cooled, and the excess LiAlH$_4$ is destroyed by very slow addition of 200 ml of water. After filtering, the organic phase is separated off. The aqueous phase is extracted with methylene chloride and this extract is added to the organic phase. After drying over Na$_2$SO$_4$ and evaporating in vacuum, 3.48 g of 1-benzyl-3-aminomethylpyrrolidine are obtained.

c) 1-Benzyl-3-(tert-butoxycarbonylaminomethyl)-pyrrolidine

A solution of 3.9 g (0.0179 mol) of di-tert-butyl dicarbonate in 8 ml of CHCl$_3$ is added very slowly and with stirring to a solution of 3.4 g (0.0179 mol) of 1-benzyl-3-aminomethylpyrrolidine in 34 ml of anhydrous CHCl$_3$ under nitrogen atmosphere. The mixture is left stirred under nitrogen overnight at ambient temperature. The solvent is evaporated in vacuum and 5.5 g of an oil are obtained, which is purified by chromatography on a column, eluted with a 98/2 CH$_2$Cl$_2$/MeOH mixture. Yield: 2.5 g (48%).

d) 3-(tert-Butoxycarbonylaminomethyl)pyrrolidine 2.1 g (0.0072 mol) of the compound obtained in stage c) above are dissolved in 30 ml of absolute ethanol. 0.3 g of Pd(OH)$_2$ on carbon (Pearlman catalyst) are added to it and hydrogenation is carried out at 45° C. and atmospheric pressure for 5 hours. The product is filtered and concentrated in vacuum, producing 1.5 g of 3-(tert-butoxycarbonylaminomethyl)pyrrolidine.

PREPARATION VI a) 1-Benzyl-3-pyrrolidinone oxime hydrochloride.

A solution of 9.7 g (0.139 mol) of hydroxylamine hydrochloride in 30 ml of water is added dropwise to a solution of 25 g (0.19 mol) of 1-benzyl-3-pyrrolidinone in 30 ml of ethanol. The materials are left at ambient temperature for 30 minutes and are heated to 35° C. for 30 minutes and concentrated at reduced pressure at 50° C. The solid product thus obtained is crystallized from isopropyl alcohol. M.p. 103°–108° C. Yield: 64.5 %.

b) 1-Benzyl-3-pyrrolidineamine.

A solution of 7.3 g (0.192 mol) of $LiAlH_4$ in 300 ml of anhydrous ethyl ether is prepared and 22 g (0.096 mol) of the compound obtained in stage a) above are added to it portionwise at ambient temperature.

The materials are left at ambient temperature for 1 hour and refluxed for 3.5 hours. The excess $LiAlH_4$ is destroyed and filtration is carried out. The filtrate is extracted with 150 ml of a 1N solution of hydrochloric acid. The solution is made basic (pH 12) and is extracted with ethyl ether. The organic phase is dried and concentrated to obtain 11 g of the product referred to above.

c) 3-Acetylamino-1-benzylpyrrolidine.

A solution of 16 g (0.178 mol) of acetic anhydride in 25 ml of ethyl acetate is added dropwise to a solution of 24 g (0.13 mol) of the compound obtained in the preceding stage in 125 ml of ethyl acetate, and the mixture is stirred for 30 minutes until the reaction has ended. The mixture is made basic by adding 134 ml of a 2N NaOH solution, the organic phase is separated off, the aqueous phase is extracted with 50 ml of ethyl acetate, the product is dried and concentrated and 150 ml of cyclohexane are added to it to obtain 11.3 g of 3-acetylamino-1-benzylpyrrolidine. M.p. 83°–85° C.

d) 3-Acetylaminopyrrolidine

A mixture of 12.5 g (0.057 mol) of the compound obtained in stage c) above, 1.3 g of 10% Pd/C, 80 ml of 95% ethanol and a drop of concentrated hydrochloric acid is hydrogenated at 40° C. When the theoretical quantity of hydrogen has been consumed, it is filtered and the filtrate is concentrated to obtain 6.5 g of the title compound in the form of an oily product.

PREPARATION VII 3-tert-Butoxycarbonylaminopyrrolidine.

The procedure of PREPARATION VI is essentially followed, the acetic anhydride in stage c) being replaced with di-tert-butyl dicarbonate and the ethyl acetate with chloroform.

PREPARATION VIII a) 6-Chloro-2-pyridinecarboxylic acid

A mixture of 3.8 g (0.03 mol) of 6-chloro-2-methylpyridine and 10.45 g of $KMnO_4$ in 380 ml of water is heated to 90° C. for 6 hours. The product is cooled, the pH is adjusted to approximately 4, water is evaporated off and the residue is taken up with ethanol. It is filtered and the ethanol is evaporated to produce 1.1 g of the compound referred to above.

b) Ethyl ester of 6-chloro-2-pyridinecarboxylic acid The compound obtained in stage a) above is heated to reflux for 3 hours in 10 ml of ethanol saturated with HCl.

The ethanol is evaporated off, the residue is taken up with ethyl acetate and is washed with a solution of sodium bicarbonate and afterwards with water. It is dried over $Na_2SO_4$ and evaporated in vacuum to obtain 0.7 g of the desired ester.

EXAMPLE 1

2-(3-Aminomethylazetidin-1-yl)-6-chloropyridine hydrochloride.

a) A mixture of 6.17 g (0.0375 mol) of the compound obtained in PREPARATION I, 5.54 g (0.0371 mol) of 2,6-dichloropyridine and 13 g (0.094 mol) of anhydrous potassium carbonate in 90 ml of n-amyl alcohol is heated to reflux temperature for 5 hours. It is cooled, filtered, and the filtrate is concentrated to dryness. The residue is ground wet in water (50 ml), filtered, and the residue is washed on the filter with water, taken up in isopropyl ether, evaporated to dryness and crystallized from 60 ml of ethyl acetate to obtain 6 g of 2-(3-acetylaminomethylazetidin-1-yl)-6-chloropyridine. M.p. 136°–138° C.

b) A mixture of 9 g (0,375 mol) of the compound obtained in stage a) above and 35.7 g (0.60 mol) of powdered potassium hydroxide in 36.6 ml of water and 183 ml of 95% ethanol is heated to reflux for 24 h. It is evaporated to a small volume, extracted with ethyl ether, the ether is evaporated off and the residue is dissolved in a mixture of 30 ml of isopropyl alcohol and 20 ml of ethyl ether. Isopropanol saturated with hydrogen chloride is added to it and the hydrochloride (4.2 g) is recovered by filtration. M.p. 200°–202° C.

EXAMPLE 2

2-(3-aminomethylazetidin-1-yl)-6-chloropyrazine dihydrochloride.

a) A mixture of 2.97 g (0.02 mol) of 2,6-dichloropyrazine, 3.72 g (0.02 mol) from the compound from PREPARATION II in free base form and 2.02 g (0.02 mol) of triethylamine in 60 ml of toluene is heated to reflux temperature for 48 hours. It is filtered hot in vacuum and the solvent is evaporated off.

b) The crude product thus obtained (4 g) is reacted at ambient temperature overnight with 25 ml of a solution of hydrochloric acid in ethanol. The precipitate is separated off by filtration and is washed with ethanol to obtain a yellow solid product (2.7 g) crystallized from ethanol by adding a few drops of water. M.p. 133°–135° C.

EXAMPLE 3

2-(3-Aminomethylazetidin-1-yl)-4-chloropyrimidine dihydrochloride

The compound referred to in the title is obtained essentially by following the procedure described in Example 2 but starting with 2,4-dichloropyrimidine instead of 2,6-dichloropyrazine. M.p. >300° C. Yield 76%.

EXAMPLE 4

2-(3-Dimethylaminomethylazetidin-1-yl)-6-chloropyridine oxalate 0.5 g (0.0025 mol) of the compound of Example 1 in free base form are dissolved in 0.5 ml of 85% formic acid (0.013 mol). 0.6 ml of 38% formaldehyde (0.08 mol) are added to it and heated to 100° C. for 1.5 hours. The mixture is adjusted to basic pH by adding a solution of NaOH, it is extracted with ethyl acetate, the combined organic extracts are dried over $Na_2SO_4$ and are concentrated at reduced pressure to obtain a yellow oil (0.45 g). This oil is dissolved in 3 ml of isopropanol and a solution of 0.25 g of oxalic acid in 1 ml of isopropanol is added to it. The mixture is heated to reflux temperature until dissolved and allowed to cool, to recover 0.4 g of the compound referred to in the title thus precipitated. M.p. 85°–90° C.

EXAMPLE 5

2-(3-Aminomethylazetidin-1-yl)-6-bromopyridine trihydrochloride a) A mixture of 8.9 g (0.04 mol) of 3-tert-butoxycarbonylaminomethylazetidine, 9.47 g (0.04 mol) of 2,6-dibromopyridine and 13.8 g (0.1 mol) of anhydrous potassium carbonate in 100 ml of dimethylsulphoxide is heated to 110° C. for 3 hours. It is poured into water, extracted with ethyl acetate, the combined organic extracts are washed with water, dried and evaporated to dryness to obtain 13 g of a yellow oil, which is purified by flash chromatography on a silica gel column by eluting with 2/8 ethyl acetate/cyclohexane. Yield of 2-(3-tert-butoxycarbonylaminomethylazetidin-1-yl)-6-bromopyridine: 4.5 g. M.p. 138°–141° C. (hexane).

b) 1 g of the latter product (0.029 mol) is treated with 10 ml of ethanol saturated with hydrogen chloride, with stirring at ambient temperature for 4 hours. It is evaporated in vacuum, taken up in isopropanol and filtered to obtain 0.85 g of the compound referred to in the title. M.p. 185°–187° C.

EXAMPLE 6

2-(3-Aminomethylazetidin-1-yl)-3-chloropyridine oxalate a) 2-(3-Acetylaminomethylazetidin-1-yl)-3-chloropyridine is obtained by following the procedure described in stage a) of Example 1, but using 2,3-dichloropyridine instead of 2,6-dichloropyridine. M.p. 109°–111° C.

b) A solution of 0.6 g (0.025 mol) of the compound obtained above in 3 ml of 6N HCl is heated to reflux for 10 hours. It is evaporated at reduced pressure and the water is removed by adding absolute ethanol and evaporating it off, twice. The residue is taken up with a very small quantity of water and made basic by adding a solution of NaOH. It is extracted with ethyl acetate, the combined organic extracts are dried over $Na_2SO_4$ and evaporated at reduced pressure to obtain 0.6 g of a yellow oil, which is dissolved in 4 ml of ethanol and acidified by adding a solution of ethanol saturated with oxalic acid. 0.3 g of the compound referred to in the title are obtained by filtration. M.p. 188°–191° C.

EXAMPLE 7

2-(3-Aminomethylazetidin-1-yl)-5-chloropyridine hydrochloride

A mixture of 0.85 g (0.0038 mol) of the compound from PREPARATION II, 0.56 g (0.0038 mol) of 2,5-dichloropyridine and 1.3 g (0.0095 mol) of anhydrous $K_2CO_3$ in 10 ml of dimethyl sulphoxide is heated with stirring to 100° C. for 4.5 hours. The mixture is poured into water, extracted twice with ethyl acetate and concentrated at reduced pressure to obtain an oily product, which is purified by chromatography on a column of silica gel by eluting with a 1/1 ethyl acetate/cyclohexane mixture. 0.32 g of a semisolid oil are thus obtained, which is dissolved in 3 ml of ethanol saturated with hydrogen chloride. After 3 hours stirring at ambient temperature the precipitate is filtered off, washed first with ethanol and then with ethyl ether and is dried to obtain 0.2 g of the compound referred to in the title. M.p. 290°–295° C. (dec.).

EXAMPLE 8

2-(3-Aminomethylazetidin-1-yl)-6-bromopyridine hydrochloride

This compound (the same as that in Example 5) is obtained also by starting with 3-acetylaminomethylazetidine, following the procedure of Example 1a) and subjecting the 2-(3-acetylaminomethylazetidin-1-yl)-6-bromopyridine thus obtained (M.p. 115°–117° C.) to an acidic hydrolysis and following essentially the procedure described in Example 1b).

EXAMPLE 9

2-(3-Aminomethyl-3-methylazetidin-1-yl)-6-chloropyridine maleate a) A mixture of 1.36 g (0.0057 mol) of the compound from PREPARATION IV, 0.85 g (0.0057 mol) of 2,6-dichloropyridine and 2.0 g (0.014 mol) of $K_2CO_3$ in 15 ml of n-pentyl alcohol is heated to reflux for 6 hours. It is cooled, the salts are removed by filtration and the material is evaporated at reduced pressure to obtain a yellow oil, which is purified by chromatography on a column of silica gel by eluting with a 95/5 methylene chloride/methanol mixture. 750 mg of 2-(3-tert-butoxycarbonylaminomethyl-3-methylazetidin-1-yl)-6-chloropyridine are thus obtained. M.p. 108°–111° C.

b) A solution of 0.7 g (0.0022 mol) of the compound obtained in stage a) above in 10 ml of ethanol saturated with hydrogen chloride is stirred overnight. The ethanol is evaporated off, the oily residue is taken up with a 10% solution of $Na_2CO_3$ and is extracted with ethyl acetate. Evaporation at reduced pressure produces 400 mg of a yellow oily product, which is dissolved in a small quantity of ethanol and precipitated in the form of maleate by adding a solution of maleic acid in ethanol. M.p. 164°–166° C. Yield: 400 mg.

EXAMPLE 10

2-(3-Methylaminomethylazetidin-1-yl)-6-chloropyridine a) A mixture of 0.56 g (0.0038 mol) of 2,6-dichloropyridine, 0.85 g (0.0038 mol) of the compound from PREPARATION II and 1.3 g (0.0095 mol) of ground anhydrous $K_2CO_3$ in 10 ml of dimethyl sulphoxide is heated to 100° C. for 4.5 hours. It is poured into water and extracted with ethyl acetate. The extract is evaporated to dryness and the residue is purified by chromatography on a column of silica gel by eluting with a 7/3 cyclohexane/ethyl acetate mixture. 0.33 g of 2-(3-tert-butoxycarbonylaminomethylazetidin-1-yl)6-chloropyridine are obtained by evaporating the fractions containing it. M.p. 124°–126° C.

b) A solution of 0.31 g (0.001 mol) of the compound obtained in stage a) above in 1 ml of tetrahydrofuran is cooled to a temperature of between 0° and 5° C. and 3 ml of a 1M solution of boranetetrahydrofuran complex are added to it. The mixture is heated to reflux overnight, is cooled, 2 ml of ethanol are added to it and the mixture is heated to reflux for 1 hour; it is cooled again, 3 ml of a solution of HCl are added and the mixture is heated to reflux for 2 hours. The product is evaporated to dryness in vacuum, the residue is taken up with absolute ethanol and evaporated to dryness in vacuum. This operation is repeated and then the residue thus obtained is chromatographed on a column of silica gel by eluting with a 7/3 ethyl acetate/methanol mixture. 0.15 g of the compound referred to in the title are recovered in the form of a yellow oil.

EXAMPLE 11

2-(3-Methylaminomethylazetidin-1-yl)-6-chloropyridine oxalate

The compound of Example 10 is prepared in the form of oxalate by the following alternative method:

a) A mixture of 1.5 g (0.0076 mol) of 2-(3-aminomethylazetidin-1-yl)-6-chloropyridine (the compound of Example 1 in free base form) and 1.1 g (0.0152 mol) of ethyl formate is heated to 85° C. for 6 hours. It is left to stand overnight and is treated with hexane and separated. The residue is evaporated to dryness, producing a semisolid oil (1.15 g) corresponding to the N-formyl derivative.

b) A 1M solution of $BH_3$-THF (12 ml) is added very slowly to a solution of 1.1 g (0.0049 mol) of the compound obtained in stage a) above in 4 ml of anhydrous tetrahydrofuran under a nitrogen atmosphere and cooled to 0° C. The mixture is heated to reflux for 4 hours, cooled to 0° C., and 6 ml of methanol are added to it very slowly dropwise. The product is heated to reflux for half an hour, is cooled, 5 ml of 5N HCl are added to it and the mixture is heated again to reflux for 90 minutes. The organic solvent is evaporated off, the aqueous phase is washed with ethyl acetate and is made basic by adding a concentrated solution of NaOH. It is extracted with ethyl acetate, the organic extract is washed with a very small quantity of water, is dried over $Na_2SO_4$ and is evaporated in vacuum. The oily product is dissolved in a small quantity of isopropanol and an excess of oxalic acid is added to it. After a few days at 2°–4° C. the compound referred to in the title is isolated by filtration. M.p. 160°–170° C.

EXAMPLE 12

6-[(3-Aminomethyl)azetidin-1-yl]-2-pyridinecarbonitrile hydrochloride a) 6-[(3-tert-Butoxycarbonylaminomethyl)azetidin-1-yl]-2-pyridinecarbonitrile A mixture of 0.2 g (0.00058 mol) of 2-bromo-6-(3-tert-butoxycarbonylaminomethyl)azetidin-1-ylpyridine obtained in stage a) of Example 5, 5 ml of anhydrous dioxane, 0.68 g (0.00058 mol) of tetrakis(triphenylphosphine)palladium, 0.22 g (0.0007 mol) of tributyltin cyanide, 0.07 g (0.0017 mol) of anhydrous LiCl and a few crystals of 2-tert-butyl-4-methylphenol is heated to reflux for 4 hours. It is cooled and 6 ml of pyridine and 20 ml of a 1.1M solution of tetrabutylammonium fluoride in tetrahydrofuran are added to it. After one night at ambient temperature it is diluted with ethyl ether and is filtered on Celite. It is concentrated, and an oily product is obtained, which is purified by chromatography by eluting with a 7/3 cyclohexane/ethyl acetate mixture. 0.06 g of the intermediate compound referred to above are obtained in the form of fluorescent solid product.

b) 6-[(3-Aminomethyl)azetidin-1-yl]-2-pyridinecarbonitrile hydrochloride.

A mixture of 0.06 g of the compound of stage a) above and 0.3 ml of trifluoroacetic acid in 3 ml of chloroform is stirred at ambient temperature overnight. It is washed with a saturated solution of $NaHCO_3$ and is extracted with ethyl acetate. The organic phase is dried over sodium sulphate and is concentrated in vacuum to obtain 0.2 g of the compound referred to in the title, in oil form. It is dissolved in a small quantity of isopropanol, acidified by adding isopropanol saturated with hydrogen chloride and the precipitate is recovered by filtration to obtain 20 mg of the compound referred to in the title. M.p. 275°–280° C.

EXAMPLE 13

6-(3-Aminomethylazetidin-1-yl)-2-aminopyridine hydrochloride a) 2-tert-Butoxycarbonylamino-6-chloropyridine. A solution of 4.36 g (0.02 mol) of di-tert-butyl dicarbonate in 10 ml of methylene chloride is added dropwise to a solution of 2.57 g (0.02 mol) of 2-amino-6-chloropyridine in 25 ml of methylene chloride. It is left at ambient temperature overnight, washed with a 1N solution of HCl and with water, and is dried over sodium sulphate and concentrated in vacuum to obtain 4.0 g of the compound referred to above, as a yellow oil.

b) 6-[(3-tert-Butoxycarbonylaminomethyl)azetidin-1-yl]-2-tert-butoxycarbonylaminopyridine.

A mixture of 1.7 g (0.0075 mol) of the compound obtained in stage a) above, 1.4 g (0.0063 mol) of 3-tert-butoxycarbonylaminomethylazetidine (PREPARATION II) and 2.2 g (0.0157 mol) of $K_2CO_3$ in 20 ml of dimethyl sulphoxide is heated to 120° C ext. overnight. 20 ml of water are added and the mixture is extracted with ethyl acetate. The organic phase is washed with water and is dried and evaporated in vacuum. The residue is purified by chromatography by eluting with a 1/9 ethyl acetate/cyclohexane mixture to obtain 1 g of the compound referred to above, which is washed with hexane.

c) 6-(3-Aminomethylazetidin-1-yl)-2-aminopyridine hydrochloride.

A mixture of 0.9 g of the compound from stage b) above and 15 ml of ethanol saturated with hydrogen chloride is stirred at ambient temperature overnight. It is evaporated to dryness to obtain the compound referred to in the title, in the form of an oily product which crystallizes when treated with 95% ethanol.

EXAMPLE 14

2-(3-Aminomethylazetidin-1-yl)-6-trifluoromethylpyridine hydrochloride a) 2-[(3-tert-Butoxycarbonylaminomethylazetidin-1-yl)-6-trifluoromethylpyridine.

A mixture of 1.55 g (0,007 mol) of 3-tert-butoxy-carbonylaminomethylazetidine (PREPARATION II), 1.52 g (0.0084 mol) of 2-chloro-6-trifluoromethylpyridine and 2.41 g (0.0175 mol) of potassium carbonate in 20 ml of dimethyl sulphoxide is heated to 120° C. ext. with stirring overnight. 30 ml of water are added, the mixture is extracted with ethyl acetate and the organic phase is washed with water, dried and evaporated in vacuum. The residue is purified by chromatography by eluting with a 7/3 cyclohexane/ethyl acetate mixture to obtain 0.95 g of the intermediate compound referred to above, in the form of white solid product.

b) 2-(3-Aminomethylazetidin-1-yl)-6-trifluoromethyl-pyridine hydrochloride.

A solution of 0.95 g of the compound obtained in the preceding stage in 12 ml of ethanol saturated with hydrogen chloride is stirred at ambient temperature for 3 hours. The ethanol is evaporated off, the oily residue thus obtained is taken up with isopropanol and the product of the title is crystallized by refrigerating. 0.35 g are obtained. M.p. 149°–151° C.

EXAMPLE 15

2-(3-Aminomethylazetidin-1-yl)-6-methoxypyridine hydrochloride a) 2-[(3-tert-Butoxycarbonylaminomethylazetidin-1-yl)-6-methoxypyridine.

The procedure of stage a) of Example 16 is followed essentially by employing 1.2 g of 2-chloro-6-methoxypyridine instead of 2-chloro-6-trifluoro-methylpyridine and the intermediate product referred to above is obtained in the form of oil.

b) 2-(3-Aminomethylazetidin-1-yl)-6-methoxypyridine hydrochloride.

The procedure of stage b) of Example 16 is followed, but starting with the intermediate compound obtained in stage a) above and the compound referred to in the title is obtained. M.p. 160°–165° C.

EXAMPLE 16

2-(3-Aminomethylazetidin-1-yl)-3-chloropyridine hydrochloride a) 2-[(3-tert-Butoxycarbonylaminomethylazetidin-1-yl)-3-chloropyridine.

A mixture of 0.85 g (0.0038 mol) of the compound from PREPARATION II, 0.56 g (0.0038 mol) of 2,3-dichloropyridine and 1.3 g (0.0095 mol) of potassium carbonate in 10 ml of dimethyl sulphoxide is heated to 110° C. ext. for 4.5 hours. It is poured into water and extracted with ethyl acetate. The organic phase is dried over sodium sulphate, is concentrated in vacuum, and the residue is purified by chromatography to obtain 0.7 g of the intermediate product referred to above.

b) 2-(3-Aminomethylazetidin-1-yl)-3-chloropyridine hydrochloride.

The product obtained in stage a) is dissolved in 70 ml of ethanol saturated with hydrogen chloride. It is stirred at ambient temperature for 3 hours, the ethanol is evaporated off, the product is taken up with a few milliliters of hot isopropanol and is cooled and filtered to obtain 0.45 g of the compound referred to in the title. M.p. 187°–192° C.

EXAMPLE 17

2-(3-Aminomethylazetidin-1-yl)-6-methylpyridine hydrochloride a) 2-[(3-tert-Butoxycarbonylaminomethylazetidin-1-yl)-6-methylpyridine.

A mixture of 2.9 g (0.013 mol) of the compound from PREPARATION II, 2.2 ml (0.0195 mol) of 2-chloro-6-methylpyridine and 4.5 g (0.0325 mol) of anhydrous potassium carbonate in 35 ml of dimethyl sulphoxide is heated to 120° C. for 6 hours. 50 ml of water are added, the mixture is extracted with ethyl acetate, the organic phase is washed with water and is dried over sodium sulphate and evaporated at reduced pressure. The oily residue is purified by chromatography by eluting with a 7/3 cyclohexane/ethyl acetate mixture to obtain 0.46 g of the product referred to above.

b) 2-(3-Aminomethylazetidin-1-yl)-6-methylpyridine hydrochloride.

0.46 g (0.0016 mol) of the compound obtained in stage a) above are dissolved in 4 ml of ethanol saturated with hydrogen chloride and left at ambient temperature for 3 hours. A small quantity of isopropanol is added to it and the material is filtered. The solid product is washed with ethyl ether and is dried to obtain 350 mg of the compound referred to in the title. M.p. 300°–310° C. (dec.).

EXAMPLE 18

6-[(3-Aminomethyl)azetidin-1-yl]-2-pyridinecarbonitrile oxalate

The compound of Example 10 is prepared in the form of oxalate by the following alternative method:

A mixture of 7.3 g (0.052 mol) of 6-chloro-pyridine-2-carbonitrile (CAS 103:71164n), 8.31 g (0.052 mol) of 3-aminomethylazetidine dihydrochloride and 25 g of anhydrous $K_2CO_3$ in 130 ml of dimethyl sulphoxide is heated to 80°–85° C. overnight.

It is filtered, evaporated at reduced pressure at 70°–80° C. and the residue is purified by chromatography on a column by eluting with methanol. On evaporating the solvent, 3.8 g of the free base are obtained, which is dissolved in a small quantity of acetone and precipitated in the form of oxalate by adding an excess of oxalic acid. M.p. 185°–190° C.

EXAMPLE 19

Hydrochloride of the ethyl ester of 6-(3-aminomethyl-azetidin-1-yl)-2-pyridinecarboxylic acid a) A mixture of 3.15 g (0.0092 mol) of the compound obtained in stage a) of EXAMPLE 5, 3.7 g (0.00117 mol) of tributylvinyltin, 1.16 g (0.027 mol) of anhydrous LiCl, 0.2 g (0.00018 mol) of tetrakis(triphenylphosphine)palladium and a very small quantity of 2-tert-butyl-4-methylphenol in 54 ml of anhydrous dioxane is heated to reflux for 3 hours. It is left to cool and 6 ml of pyridine and 15 ml of a 1.1M solution of tetrabutylammonium chloride in tetrahydrofuran are added to it. After stirring overnight, 100 ml of ethyl ether are added and the mixture is filtered on Celite. The organic solution is evaporated to dryness to obtain 2-(3-tert-butoxycarbonylaminomethylazetidin-1-yl)-6-vinylpyridine in the form of a yellow oil, which is crystallized from hexane (2.4 g). M.p. 85°–87° C.

b) 6.8 g (0.031 mol) of sodium periodate are added to a mixture of 3.1 g (0.01 mol) of the compound obtained above, 0.07 g (0.00028 mol) of osmium tetraoxide, 80 ml of tetrahydrofuran and 23 ml of water and are stirred at ambient temperature for 3 hours. The product is poured into 120 ml of water, extracted with ethyl acetate, the organic phase is washed with water and is dried over sodium sulphate, is filtered and is evaporated to dryness. A yellow oil (3 g) is obtained which, after crystallization on adding a small quantity of ethyl ether, gives 2.2 g of 6-(tertbutoxycarbonylaminomethylazetidin-1-yl)-2-pyridinecarboxaldehyde. M.p. 125°–127° C.

c) A solution of 10.3 g of 80% $NaClO_2$ and 9.2 g of $NaH_2PO_4$ in 55 ml of distilled water is added to a solution of the compound obtained in stage b) above in 150 ml of tert-butanol and is stirred at ambient temperature for 1 hour. 120 ml of water are then added and the mixture is extracted with ethyl acetate. The organic extract is dried over sodium sulphate and filtered and is evaporated to dryness to obtain a yellow oil corresponding to 6-(3-tert-butoxycarbonylaminomethylazetidin-1-yl)-2-pyridine carboxylic acid, which is purified by chromatography on a column by eluting with a 7/3 ethyl acetate/methanol mixture.

d) A mixture of 1.9 g of the compound obtained in stage c) above and 10 ml of absolute ethanol saturated with hydrogen chloride is stirred at ambient temperature overnight; it is then evaporated to dryness, 15 ml of ethanol saturated with hydrogen chloride are added and the mixture is heated to reflux for 3 hours. It is evaporated to dryness, the residue is taken up with 50 ml of ethyl acetate and 20 ml of an aqueous solution of sodium bicarbonate, the organic phase is separated off and is then washed with water, dried and evaporated. The residue is taken up with 20 ml of acetone, the solution is acidified by adding isopropanol saturated with hydrogen chloride and the crystallized product is recovered by filtration. M.p. 118°–120° C.

EXAMPLE 20

Hydrochloride of the ethyl ester of 6-(3-aminomethyl-azetidin-1-yl)-2-pyridinecarboxylic acid The compound of Example 19 is also obtained by the following alternative method:

A mixture of 0.65 g (0.0029 mol) of the compound from Preparation II in the form of hydrochloride, 0.53 g (0.0029 mol) of the compound from preparation VIII and 1.0 g (0.00725 mol) of anhydrous $K_2CO_3$ in 8 ml of dimethyl sulphoxide is heated to 110° C. with stirring overnight. The reaction mixture is poured into water and is extracted twice with ethyl acetate. The organic phase is concentrated in vacuum and the oily residue thus obtained is purified by chromatography by eluting with a 7/3 cyclohexane/ethyl acetate mixture. The product thus obtained is dissolved in 3 ml of ethanol saturated with HCl and is left stirred at ambient temperature overnight. 30 ml of absolute ethanol are added to it, the mixture is concentrated at reduced pressure and the residue is taken up with isopropanol and the compound of the title is left to crystallize and is then isolated by filtration. Yield 0.16 g. M.p. 119°–121° C.

EXAMPLE 21

6-[(3-Aminomethyl)azetidin-1-yl]-2-pyridinecarboxamide

A mixture of 0.8 g (0.0042 mol) of the compound from Example 10, 4 ml of distilled water and 8 ml of 5N HCl is heated to reflux temperature for 4 hours and is evaporated to dryness. The residue is taken up with ethanol and the ethanol is evaporated off, this operation is repeated several times and finally the residue is taken up with isopropanol. After one night at 2°–4° C. the product is filtered, producing 0.95 g of the compound referred to in the title. M.p. 297°–303° C. A product with m.p. >310° C. is obtained by crystallization from ethanol at 90° C.

EXAMPLE 22

6-(3-Aminomethylazetidin-1-yl)-2-vinylpyridine hydrochloride 0.5 g (0.0017 mol) of the compound obtained in stage a) of Example 19 are dissolved in 5 ml of ethanol saturated with hydrogen chloride and are stirred at ambient temperature for 3 hours. The ethanol is evaporated off, the residue is taken up in isopropanol and is filtered to obtain 0.35 g of the compound referred to in the title, in the form of yellow solid. M.p. 285°–286° C.

EXAMPLE 23

6-(3-Aminomethylazetidin-1-yl)-2-pyridinecarboxaldehyde hydrochloride 0.6 g (0.002 mol) of the compound obtained in stage b) of Example 19 are dissolved in 8 ml of ethanol saturated with hydrogen chloride and are stirred at ambient temperature for 3 hours. The material is concentrated in vacuum and the product referred to in the title is obtained in the form of a dark oil.

EXAMPLE 24

2-[(3-Aminomethyl)azetidin-1-yl]-6-(1-piperidinyl)pyridine hydrochloride a) 2-[(3-tert-Butoxycarbonylaminomethyl)azetidin-1-yl]-6-(1-piperidinyl)pyridine A mixture of 0.3 mg (0.8 mmol) of the compound obtained in stage a) of Example 5, 0.1 ml (0.8 mmol) of piperidine and 0.17 g (1.2 mmol) of $K_2CO_3$ in 3 ml of dimethyl sulphoxide is heated to approximately 100° C. with stirring for 8 hours. The reaction mixture is poured into water and is extracted twice with ethyl acetate and once with methylene chloride. It is concentrated at reduced pressure and 0.4 g of an oily product is obtained, which crystallizes spontaneously.

b) 2-[(3-Aminomethyl)azetidin-1-yl]-6-(1-piperidinyl)pyridine hydrochloride

The product obtained in stage a) is dissolved in 3 ml of ethanol saturated with HCl, is left stirring at ambient temperature overnight, and the product referred to in the title is isolated by filtration.

EXAMPLE 25

2-(3-Aminopyrrolidin-1-yl)-6-chloropyrazine dihydrochloride.

a) 2-Chloro-6-(3-tert-butoxycarbonylaminopyrrolidin-1-yl)pyrazine.

A mixture of 2.24 g (0.012 mol) of the compound obtained in PREPARATION VII, 1.79 g (0.012 mol) of 2,6-dichloropyrazine and 1.2 g (0.012 mol) of triethylamine in 50 ml of toluene is heated to reflux for 24 hours. It is filtered hot to remove the salts, the solvent is evaporated off and the oily product which is obtained is purified by chromatography on a column of silica gel by eluting with a 9/1 methylene chloride/ethyl acetate mixture. 600 mg of the compound referred to above are thus obtained.

b) 6-(3-Aminopyrrolidin-1-yl)-2-chloropyrazine dihydrochloride.

The product from stage a) above is dissolved in 10 ml of ethanol saturated with hydrogen chloride and is left stirred at ambient temperature overnight. It is filtered and 0.41 g of the title compound are obtained in the form of a yellow solid product which is recrystallized from ethanol. M.p. 233°–235° C.

EXAMPLE 26

2-(3-Aminopyrrolidin-1-yl)-6-chloropyrimidine dihydrochloride.

a) 6-Chloro-2-(3-tert-butoxycarbonylaminopyrrolidin-1-yl)pyrimidine.

A mixture of 2.77 g (0.015 mol) of 3-tert-butoxycarbonylaminopyrrolidine (PREPARATION VII), 2.21 g (0.015 mol) of 2,6-dichloropyrimidine and 1.5 g (0.013 mol) of triethylamine in 50 ml of toluene is heated to reflux for 48 hours. It is allowed to cool, filtered and the filtrate is evaporated to dryness to obtain a crude product, which is purified by chromatography on a column of silica gel by eluting with a 98/2 methylene chloride/methanol mixture. 800 mg of the compound referred to above are obtained. M.p. 97°–98° C.

b) 2-(3-Aminopyrrolidin-1-yl)-6-chloropyrimidine dihydrochloride.

The compound obtained in stage a) above is dissolved in 10 ml of ethanol saturated with hydrogen chloride and is stirred at ambient temperature overnight. The precipitate is filtered off and is then crystallized from absolute ethanol to obtain 0.56 g of the compound referred to in the title. M.p. >330° C.

EXAMPLE 27

2-(3-Aminopyrrolidin-1-yl)-6-chloropyridine hydrochloride a) 2-(3-Acetylaminopyrrolidin-1-yl)-6chloropyridine.

A mixture of 4.8 g (0.0375 mol) of the compound obtained in PREPARATION VI, 5.54 g (0.0371 mol) of 2,6-dichloropyridine and 6.5 g (0.047 mol) of anhydrous potassium carbonate in 90 ml of n-amyl alcohol is heated to reflux for 5 hours. It is cooled, filtered and the filtrate is concentrated to dryness. The residue is ground wet in water (50 ml), is filtered, the residue is washed on the filter with water, is taken up in isopropyl ether, the solution is evaporated to dryness and the product is crystallized from 60 ml of ethyl acetate to obtain 5.7 g of the compound referred to above.

b) 2-(3-Aminopyrrolidin-1-yl)-6-chloropyridine hydrochloride.

A mixture of 4.46 g (0.187 mol) of the compound obtained in stage a) above and 17.8 g (0.30 mol) of powdered potassium hydroxide in 18.3 ml of water and 90 ml of 95% ethanol is heated to reflux for 24 hours. It is evaporated to a small volume, extracted with ethyl ether, the ether is evaporated off and the residue is dissolved in a mixture of 15 ml of isopropyl alcohol and 10 ml of ethyl ether. Isopropanol saturated with hydrogen chloride is added to it and the hydrochloride (2.3 g) is recovered by filtration. M.p. 258°–260° C.

EXAMPLES 28–33

By essentially following the procedure of Example 25, but replacing 2,6-dichloropyrazine with 2,6-dibromopyridine, 2,3-dichloropyridine, 2,5-dichloropyridine, 2-chloro-6-trifluoromethylpyridine, 2-chloro-6-methoxypyridine and 2-chloro-6-methylpyridine the following are obtained, respectively: 2-(3-aminopyrrolidin-1-yl)-6-bromopyridine (Ex. 28), 2-(3-aminopyrrolidin-1-yl)-3-chloropyridine (Ex. 29), 2-(3-aminopyrrolidin-1-yl)-5-chloropyridine (Ex. 30), 2-(3-aminopyrrolidin-1-yl)-6-trifluoromethylpyridine (Ex. 31), 2-(3-aminopyrrolidin-1-yl)-6-methoxypyridine (Ex. 32), 2-(3-aminopyrrolidin-1-yl)-6-methylpyridine (Ex. 33), in the form of addition salts with hydrochloric acid.

EXAMPLE 34

2-(3-Amino-3-methylpyrrolidin-1-yl)-6-chloropyridine hydrochloride 2-(3-Amino-3-methylpyrrolidin-1-yl)-6-chloropyridine hydrochloride is obtained by following the procedure of Example 27 but employing 3-acetylamino-3-methylpyrrolidine described in EP-132845 ("Reference Example 7") instead of the compound from the PREPARATION VI, in stage a).

EXAMPLE 35

2-(3-Dimethylaminopyrrolidin-1-yl)-6-chloropyridine oxalate 0.25 g (0.00127 mol) of the compound from Example 27 in free base form are dissolved in 0.25 ml of 85% formic acid (0.00564 mol). 0.3 ml of 38% formaldehyde (0.04 mol) are added to it and the mixture is heated to 100° C. for 2 hours. It is made basic with the aid of a solution of NaOH and is extracted with ethyl acetate. The organic extracts are dried and the solvent is evaporated off in vacuum. The residue is dissolved in a small quantity of isopropanol and a solution of oxalic acid in isopropanol is added to it when hot. The mixture is allowed to cool and the product referred to in the title is recovered by filtration.

EXAMPLE 36

2-(3-Aminopyrrolidin-1-yl)-6-vinylpyridine hydrochloride a) 2-(3-tert-Butoxycarbonylaminopyrrolidin-1-yl)-6-vinylpyridine.

The compound referred to above is obtained essentially by following the procedure described in stage a) of Example 19 but starting with 2-(3-tert-butoxycarbonylaminopyrrolidin-1-yl)-6-bromopyridine, obtained by reaction of 2,6-dibromopyridine with the compound from PREPARATION VII, instead of 2-(3-tert-butoxycarbonylaminomethylazetidin-1-yl)-6-bromopyridine.

b) 2-(3-Aminopyrrolidin-1-yl)-6-vinylpyridine hydrochloride

The compound referred to in the title is obtained from the compound obtained in stage a) above and by following the procedure of Example 22.

EXAMPLE 37

Hydrochloride of the ethyl ester of 6-(3-aminopyrrolidin-1-yl)-2-pyridinecarboxylic acid The compound referred to above is obtained by following the procedure of Example 20 but replacing the compound from PREPARATION II with 3-tert-butoxycarbonylaminopyrrolidine.

EXAMPLE 38

6-(3-Aminopyrrolidin-1-yl)-2-pyridinecarbonitrile oxalate

The compound referred to in the title is obtained essentially by following the procedure of Example 20 but replacing 3-aminomethylazetidine dihydrochloride with 3-aminopyrrolidine dihydrochloride obtained from the compound from PREPARATION VI by hydrolysis.

EXAMPLE 39

2-[(3-Aminomethyl)pyrrolidin-1-yl]-6-chloropyridine hydrochloride

A mixture of 1.5 g (0.0075 mol) of the compound from PREPARATION V, 1.12 g (0.0075 mol) of 2,6-dichloropyridine and 2.5 g (0.0184 mol) of $K_2CO_3$ in 15 ml of n-amyl alcohol is heated to reflux temperature for 6 hours. It is cooled, the salts are filtered off and the solvent is evaporated

We claim:

1. 1-Heteroarylazetidine or -pyrrolidine of formula (I)

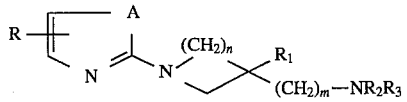

in which

A denotes a —CH=CH— group;

R denotes a hydrogen atom, a halogen atom, a $C_1$–$C_4$ alkyl, $C_1$–$C_4$ alkoxy or $C_1$–$C_4$ alkylthio group, a cyano, carboxamido, trifluoromethyl, vinyl or formyl group, a carboxyl group in free, salt or esterified form, a hydroxyl, hydroxymethyl or mercapto group or an amino, mono- or di($C_1$–$C_4$ alkyl)amino, aminomethyl, mono- or di($C_1$–$C_4$ alkyl)aminomethyl, 1-piperidino, 1-pyrrolidino, 1-piperazino or 4-($C_1$–$C_4$ alkyl)-1-piperazino group, it being possible for this group R to replace any one of the hydrogen atoms of the heteroaryl nucleus;

$R_1$ is a hydrogen atom or a methyl group;

$R_2$ and $R_3$ which are identical or different, denote a hydrogen atom or a $C_1$–$C_4$ alkyl group;

n is 1 or 2, m is 0 or 1 and $m+n \geq 2$ and its addition salts with inorganic or organic acids.

2. 1-Heteroarylazetidine according to claim 1, where n=m=1 of formula (Ia)

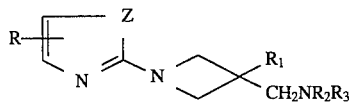

in which A, R, $R_1$, $R_2$ and $R_3$ are as defined in claim 1, and its addition salts with acids.

3. 1-Heteroarylpyrrolidine according to claim 1 where n=2 of formula (Ib)

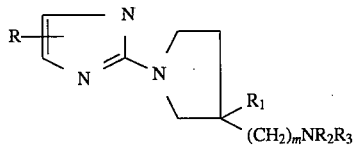

in which m, A, R, $R_1$, $R_2$ and $R_3$ are as defined in claim 1, and its addition salts with acids.

4. 1-Heteroarylazetidine of claim 2, where $R_1$ is hydrogen, and its addition salts with acids.

5. 1-Heteroarylazetidine of claim 4, where R denotes a hydrogen or halogen atom, a $C_1$–$C_4$ alkyl, $C_1$–$C_4$ alkoxy, cyano, carboxamido, trifluoromethyl, vinyl, formyl, carboxyl in free, salt or esterified form, or amino group and its addition salts with acids.

6. 1-Heteroarylazetidine of claim 5, where R denotes a chlorine or bromine atom in positions 3, 5 or 6, and $R_2$ and $R_3$ are identical and denote a hydrogen atom or a $C_1$–$C_4$ alkyl group, and its addition salts with acids.

7. 1-Heteroarylpyrrolidine of claim 3, where $R_1$ is a hydrogen atom and its addition salts with acids.

8. 1-Heteroarylpyrrolidine of claim 7, where R denotes a hydrogen atom, a halogen atom, a $C_1$–$C_4$ alkyl, $C_1$–$C_4$ alkoxy, cyano, carboxamido, trifluoromethyl, vinyl, formyl, carboxyl in free, salt or esterified form or amino group and its addition salts with acids.

9. 1-Heteroarylpyrrolidine of claim 8, where R denotes a chlorine or bromine atom in positions 3, 5 or 6, m is 0, and $R_2$ and $R_3$ are identical and denote a hydrogen atom or a $C_1$–$C_4$ alkyl group, and its addition salts with acids.

10. A pharmaceutical composition comprising as active principle at least one 1-heteroarylazetidine, 1-heteroarylpyrrolidine or addition salts thereof with pharmaceutically acceptable acids, as claimed in claim 1, in combination with a pharmaceutically acceptable carrier.

11. A pharmaceutical composition comprising as active principle at least one 1-heteroarylazetidine or acid addition salts thereof, as claimed in claim 2, in combination with a pharmaceutically acceptable carrier.

12. A pharmaceutical composition comprising as active principle at least one 1-heteroarylpyrrolidine or acid addition salts thereof, as claimed in claim 3, in combination with a pharmaceutically acceptable carrier.

13. A method for the treatment or prophylaxis of disorders which involve the peripheral or the central serotoninergic system when it is desired to have a selective agonist action mediated by serotonin 5-$HT_3$ receptors, which comprises administering to a subject an effective amount of a 1-heteroarylazetidine or 1-heteroarylpyrrolidine, or acid addition salts thereof, as claimed in claim 1.

14. A method for the treatment or prophylaxis of disorders which involve the peripheral or the central serotoninergic system when it is desired to have a selective agonist action mediated by serotonin 5-$HT_3$ receptors, which comprises administering to a subject an effective amount of a 1-heteroarylazetidine or acid addition salts thereof, as claimed in claim 2.

15. A method for the treatment or prophylaxis of disorders which involve the peripheral or the central serotoninergic system when it is desired to have a selective agonist action mediated by serotonin 5-$HT_3$ receptors, which comprises administering to a subject an effective amount of a 1-heteroarylpyrrolidine or acid addition salts thereof, as claimed in claim 3.

16. A method for the treatment or prophylaxis of dysthymic disorders, of psychotic disorders, of cases of anxiety, or of constipation, which comprises administering to a subject an effective amount of a 1-heteroarylazetidine or 1-heteroarylpyrrolidine, or acid addition salts thereof, as claimed in claim 1.

17. A method for the treatment or prophylaxis of dysthymic disorders, of psychotic disorders, of cases of anxiety, or of constipation, which comprises administering to a subject an effective amount of a 1-heteroarylazetidine or acid addition salts thereof, as claimed in claim 2.

18. A method for the treatment or prophylaxis of dysthymic disorders, of psychotic disorders, of cases of anxiety, or of constipation, which comprises administering to a subject an effective amount of a 1-heteroarylpyrrolidine or acid addition salts thereof, as claimed in claim 3.

* * * * *